(12) United States Patent
Correa (10) Patent No.: US 6,537,824 B1
(45) Date of Patent: Mar. 25, 2003

(54) PROCESS FOR METERING HYDROGEN PERMEATED IN A METALLURGICAL STRUCTURE, AND APPARATUS THEREOF

(76) Inventor: Luiz Augusto Demaria Correa, Travessa Joãn°72 ap. 61 - Batel - 80.240-100, Curitiba - PR (BR)

( * ) Notice: Subject to any disclaimer, the term of this patent is extended or adjusted under 35 U.S.C. 154(b) by 0 days.

(21) Appl. No.: 09/473,917

(22) Filed: Dec. 28, 1999

(51) Int. Cl.$^7$ ............................................. G01N 17/00
(52) U.S. Cl. ...................... 436/144; 423/700; 422/53; 436/151
(58) Field of Search ................ 422/53, 55; 324/700; 204/404; 205/775.5; 436/6, 151, 141

(56) References Cited

U.S. PATENT DOCUMENTS

| | | | | |
|---|---|---|---|---|
| 3,631,338 A | * | 12/1971 | Fitzpatrick | 205/775.5 |
| 4,863,572 A | * | 9/1989 | Jasinski | 204/404 |
| 5,338,432 A | * | 8/1994 | Agarwala et al. | 205/118 |
| 6,077,418 A | * | 6/2000 | Iseri et al. | 205/775.5 |

* cited by examiner

Primary Examiner—Jill Warden
Assistant Examiner—Sam P. Siefke (74) Attorney, Agent, or Firm—The Kline Law Firm (57) ABSTRACT

Patent of invention "PROCESS FOR METERING HYDROGEN PERMEATED IN A METALLURGICAL STRUCTURE, AND APPARATUS THEREOF", refers to a process for metering permeated hydrogen flow in machines, equipment, piping, or other metallic apparatus, used in the oil industry, refineries, chemical industries, petrochemical industries, units for production, pumping, transport, and storage of petroleum and gas, tanks, machines, and equipment that work with hydrogen, or chemicals that can generate hydrogen, and nuclear industries, through a sensor that uses the properties of a couple of dissimilar materials, in construction and installation that are suitable to measure electrical values between a metering couple and a reference couple. The measured value is a function of the flow rate of hydrogen that permeates the metallic surface under monitoring. In consequence, we obtain a process for measuring hydrogen corrosion or hydrogen flow through an apparatus having a low cost of construction, an unlimited shelf life, not wasting any materials, a high response velocity, an accuracy and precision that are equivalent or better than those obtained by the state-of-art methods, and a extremely simple and cheap installation, a low cost of maintenance, with an easy integration with process computers, either digital or analogic.

4 Claims, 6 Drawing Sheets

PROCESS FOR METERING HYDROGEN PERMEATED IN A METALLURGICAL STRUCTURE, AND APPARATUS THEREOF

BACKGROUND OF THE INVENTION

1. Field of the Invention

The present invention is a process for metering permeated hydrogen flow in machines, equipment, piping, or other metallic apparatus, used in the oil industry, refineries, chemical industries, petrochemical industries, units for production, pumping, transport, and storage of petroleum and gas, tanks, machines, and equipment that work with hydrogen, or chemicals that can generate hydrogen, and nuclear industries. The system uses a sensor that uses the properties of a couple of dissimilar materials that are, in construction and installation, suitable to measure electrical values between a metering couple and a reference couple. The measured value is a function of the flow rate of hydrogen that permeates the metallic surface being monitored. In consequence, we obtain a process for measuring hydrogen corrosion or hydrogen flow through an apparatus that has a low cost of construction, an unlimited shelf life, does not waste any materials, has a high response velocity, and has an accuracy and precision that are equivalent to or better than those obtained by the state-of-art methods. The system is extremely simple and cheap to install, and has a low cost of maintenance, and is easily integrated with process computers.

2. Description of the Prior Art

As is well known in the field of Industrial Corrosion sector, structural damage is caused, in many cases, by the intrusion of hydrogen in a metallic structure. The hydrogen is generated by acidic means containing free protons ($H^+$cation), through chemical processes that lead to proton formation, by atomic hydrogen ($H^0$) formation, or even by hydrogen gas ($H_2$) being adsorbed in the metallic structure. The structural damage caused by the hydrogen is quite varied, and includes hydrogen-induced cracking (HIC), sulfur stress cracking (SSC), and Stress Oriented Hydrogen Induced Cracking (SOHIC). Several processes have been conceived for controlling these problems, such as forming a layer of protective material, controlling the conditions of the fluid in contact with the material submitted to corrosion, etc. However, a key problem is how to measure, in a safe, economically viable, and quick way, the hydrogen formation next to a corrosion-subjected surface. Great efforts have been made to obtain a hydrogen sensor with a faster response time, with easy installation, the least possible maintenance, with precise and accurate results, with integration to data processing systems, and, of course, the least possible cost.

Figure 4:
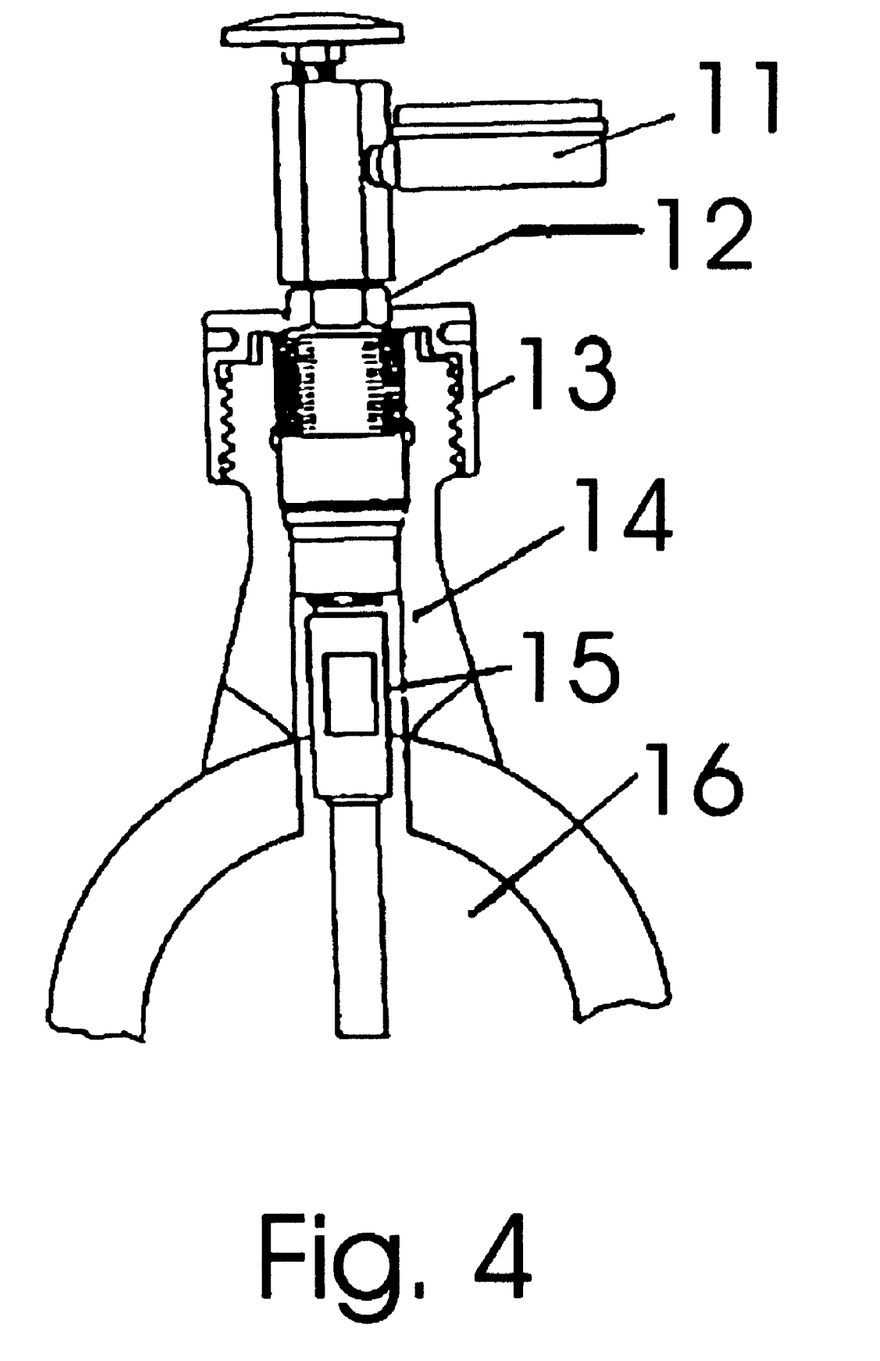
FIG. 4 shows a typical pressure sensor by insertion.

Current arat sensors for hydrogen permeated in metallic structures can be classified into 4 groups: Pressure sensors, vacuum sensors, electrochemical sensors, and fuel cell sensors as described below:

1. Pressure sensors are based on measuring the pressure generated by gaseous hydrogen ($H_2$), formed by the combination between hydrogen atoms ($H_0$), when these atoms cross the hydrogen-permeated surface, or the walls of a reaction tube inserted in the hydrogen generating means. These sensors can be of 2 types:

1.1 Pressure sensors by insertion: This model is made of a thin-walled carbon steel pipe (reactional tube), which has one of its ends closed, while the other end is in communication with a pressure meter, the meter being inserted into the hydrogen generating means. In FIG. 4, we can see a typical pressure sensor by insertion, which has a pressure meter (11), typically a manometer, a connection (12), an external body (13 & 14), a reaction tube (15), inserted in the hydrogen generating means (16). Atomic hydrogen ($H^0$), formed by corrosion reactions out of the wall of reactional tube (15), cross this wall and then changes to molecular hydrogen gas ($H_2$), with a molecular volume greater than $H^0$. The gas can therefore not return to the hydrogen generator means, and thus accumulates inside the tube, raising the tube internal pressure, which is measured by the pressure meter (11). That sensor allows checking the efficiency of corrosion inhibitors based on the suppression of hydrogen formation, having pressure stabilization when an inhibitor is effective. However, these sensors do not have a quick response time (it can even take one month to attain measurable levels), nor great sensitivity. In addition, these sensors are difficult to integrate with process computers.

Figure 5:
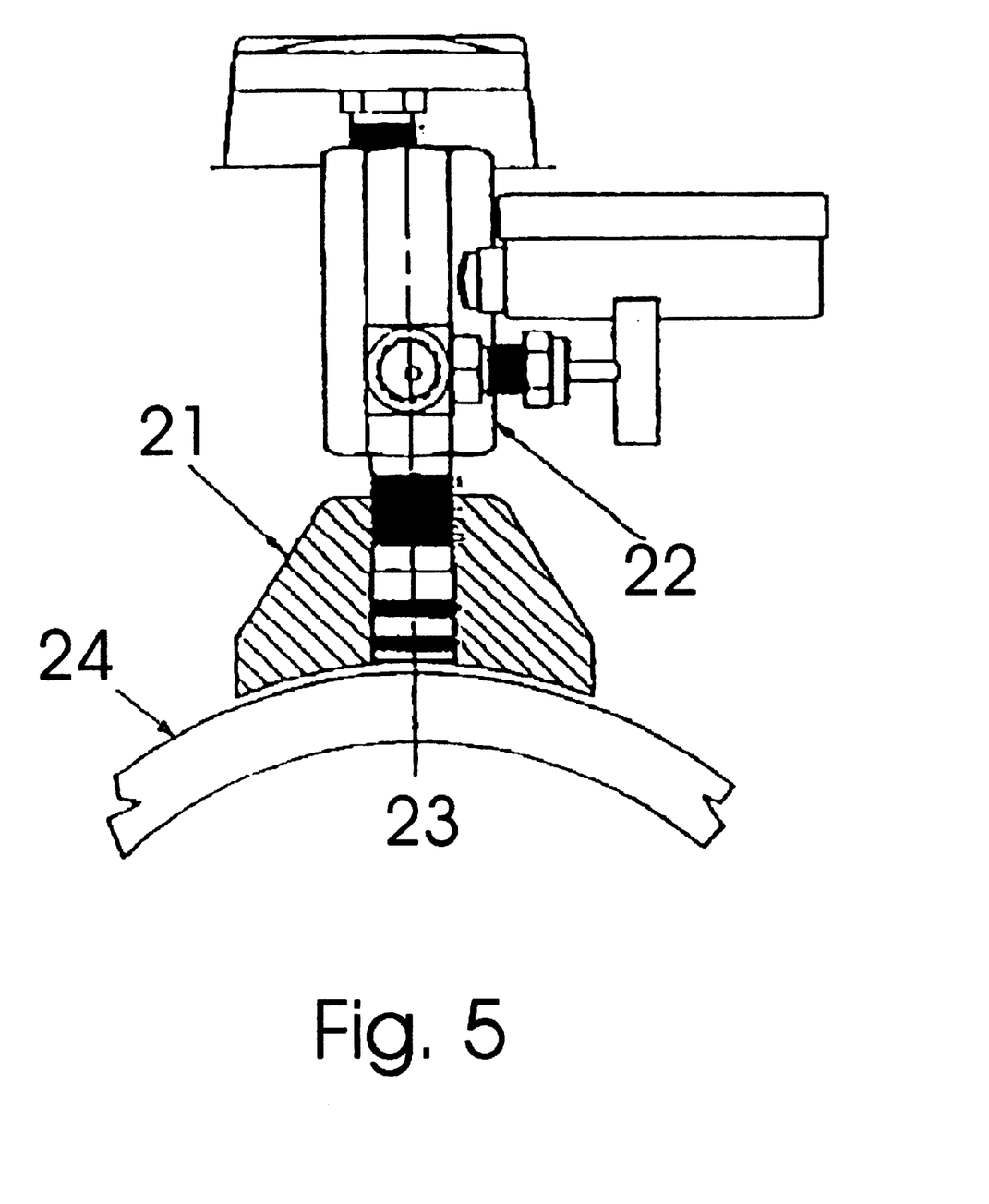
FIG. 5 shows a typical external pressure sensor.

1.2 External pressure sensors: This model of sensor works similarly to those described above, but the sensor is installed externally, forming a chamber between the external wall of the corrosion-subjected surface and the sensor, where molecular hydrogen ($H_2$) accumulates, giving rise to the pressure increase, in the same way as in insertion-type sensors. In FIG. 5, a typical external pressure sensor is shown, with an external coupling (21), a manometer-thermometer assembly (22), a pressurizing chamber (23), with this assembly being coupled directly to the surface under corrosion by hydrogen (24). This sensor has the advantage, over the insertion-type sensor described in item 1.1, that it can be assembled externally to the corrosion-subjected surface, without interference on the industrial process. However, the system response time is even slower, due to the greater thickness of the corrosion-subjected walls, when compared with the wall thickness of the reaction tube from the insertion-type sensors. The system also suffers the other shortcomings of the insertion-type sensors.

2. Vacuum-type sensors: These sensors are based on the changing in the grid current of a vacuum electronic valve, when its exterior side, made in steel, suffers corrosion by hydrogen, this current being proportional to the mass of hydrogen coming into the tube. They can be installed externally to the surface under corrosion as well as through insertion in the corrosive means, and have been greatly improved ultimately, having, over the pressure sensors, the advantage of a greater sensitivity. State-of-the-art Vacuum sensors work with the hydrogen-collecting cavity under high vacuum ($10^{-6}$ Pa), and they can measure hydrogen masses as low as $10^{-9}$ g. In spite of its greater sensitivity, however, vacuum sensors are indicated only for laboratory work, or in industrial units with a very controlled environment, like, for example, in nuclear plants, due to its electronics and hardware being very expensive and fragile for the rough working conditions of an oil plant.

Figure 6:
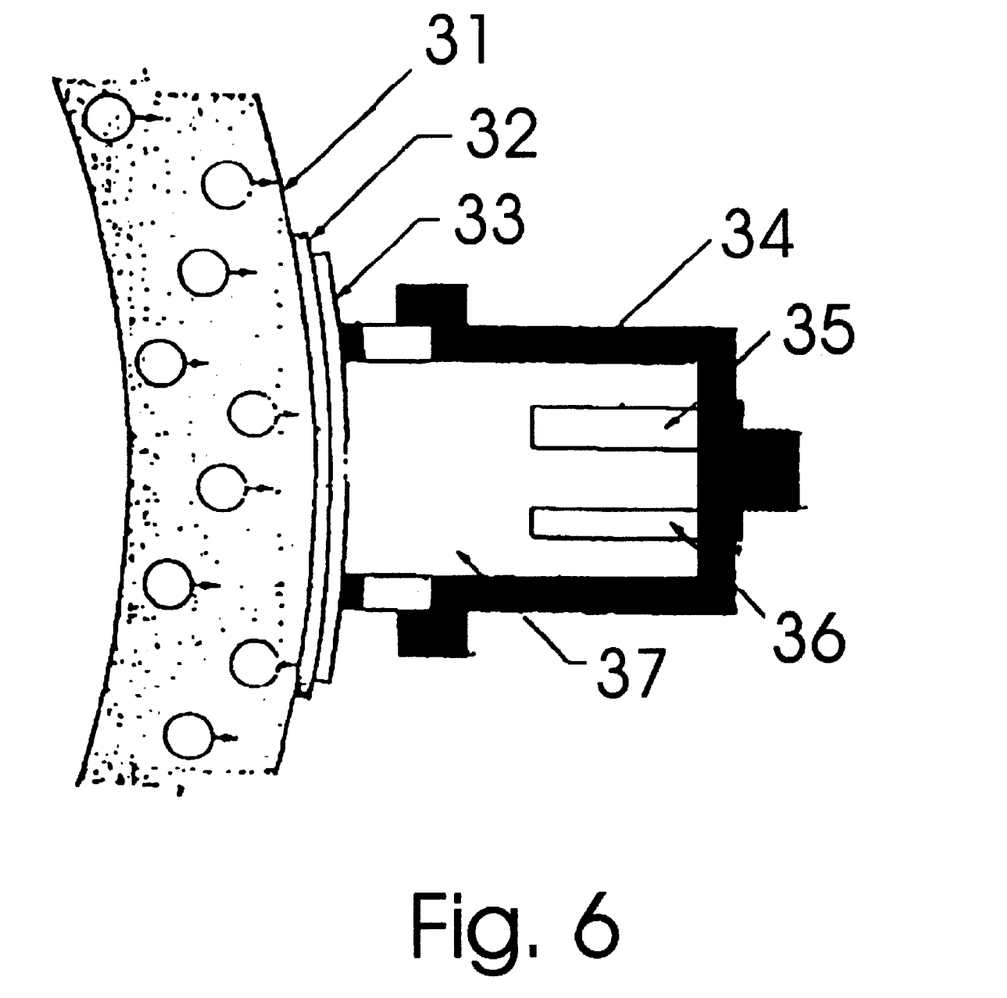
FIG. 6 shows a typical palladium electrochemical sensor.

3. Electrochemical sensors: Beginning from the work of Devanathan et alii, which aimed at first to determine diffusivity of hydrogen through metallic plates, using an electrochemical double cell, in which the metal test-piece was the surface separating the semi-cells each other, electrochemical sensors were developed based on the oxidation of atomic hydrogen ($H^0$) and electrochemical reduction of the formed ionic hydrogen ($H^+$) producing molecular hydrogen ($H_2$), the electrical current from that oxidation being proportional to the mass of permeated hydrogen. A commercial example of this type of sensor is shown in FIG. 6. In this model, atomic hydrogen (31) that permeates the corrosion-subjected surface (32) is oxidized when permeating a palladium metal sheet (33), polarized by a potentiostate, forming hydrogen cathion ($H^+$) when entering into contact with the electrolyte (34). The hydrogen cation produced is then reduced in the auxiliary electrode (35), forming molecular hydrogen. In this model, the main disadvantage is the use of a noble metal (palladium), with the necessary cost increase. Electrochemical sensors are generally of complex construction, need expensive measurement instruments, have a low response velocity, need an external assembly, and have the additional disadvantage of a limited shelf life. In addition, the electrochemical processes can be very complicated, being subject to interference by generator means and electrolytes contaminants, by the temperature, etc. Several variants have been recently developed, such as solid electrolyte sensors, but none of these efforts actually eliminated the cited disadvantages.

Figure 7:
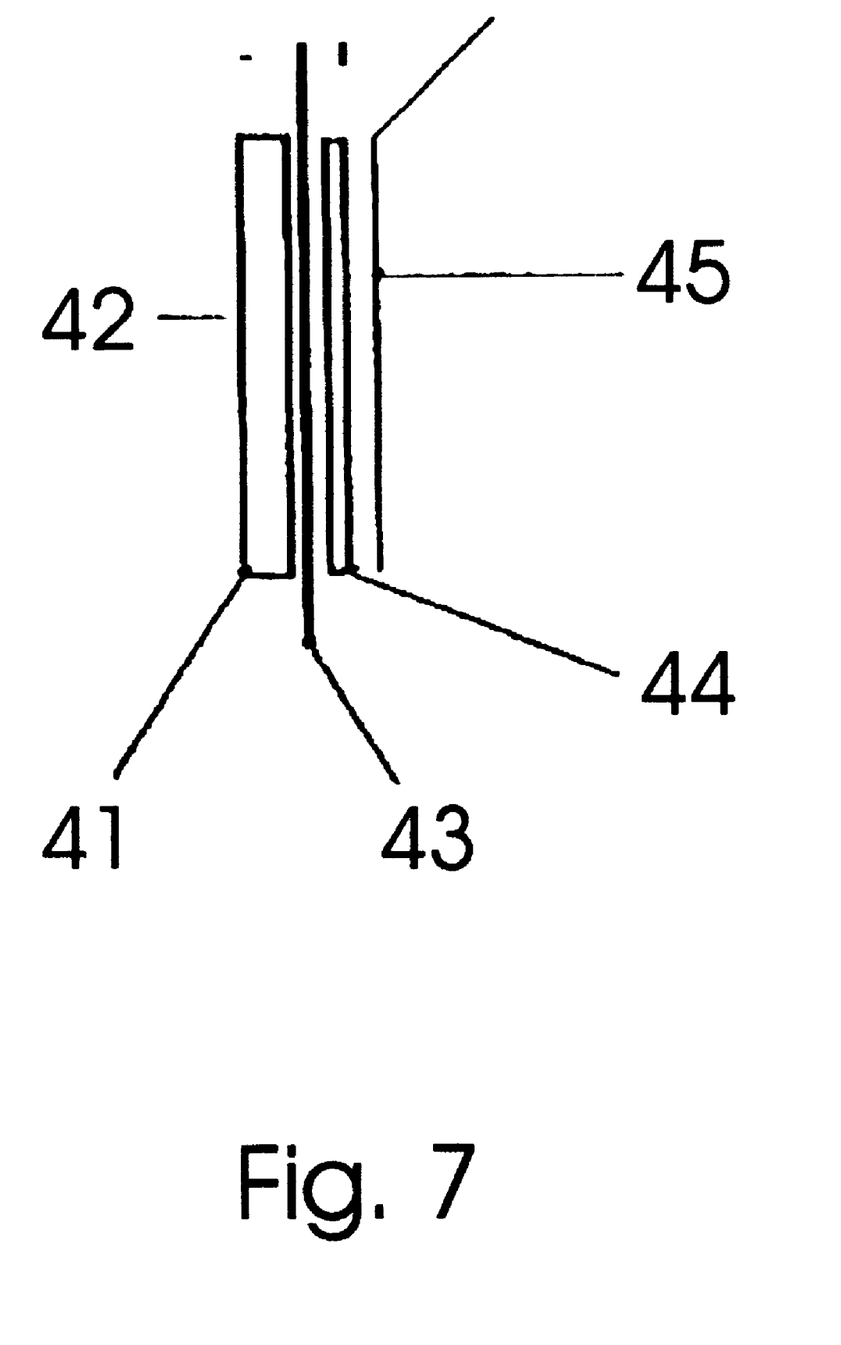
FIG. 7 shows a fuel cell sensor.

4. Fuel cell sensors: This type of sensor makes use of the fuel cell principle, where there is electrical current generation when the hydrogen generated by the corrosive means crosses over the surface under corrosion (anode) in the atomic form ($H^0$), and is transformed in ionic hydrogen ($H^+$) by entering in contact with an electrolyte, and then reacts with oxygen from the air in a porous cathode, forming water and thus generating the electrical current. Once each hydrogen atom provides one electron, that current is proportional to the flow of hydrogen by the surface. An example of this type of sensor, utilizing as the solid electrolyte a proton-exchange membrane of perfluorinated sulphonic acid, is seen in FIG. 7, where the corrosion-subjected surface whose hydrogen flow is to be measured (41) corresponds to the fuel cell anode, the point of admittance of hydrogen (42), the membrane-type solid electrolyte (43), the porous electrolyte (44), that catches oxygen from the air and corresponds to the cathode from the fuel cell, and the current collector (45), which is electrically connected, as well as the material under corrosion (41), to a microamperimeter for measuring the electrical current proportional to hydrogen flow. In order to obtain the greatest possible transport of oxygen from the air, the cathode is made from graphite pressed with platinum particles with a large contact surface, making the sensor expensive. Besides that, the mechanical construction is relatively complex, raising the cost for manufacturing of this model. Finally, this type of sensor does not actually eliminate the disadvantages of the electrochemical sensors, as it requires an external assemblage, with consequent delay in response time, and complex and expensive measuring instruments.

SUMMARY OF THE INVENTION

The present invention was developed to overcome the disadvantages of the sensors and processes now in use by utilizing the concepts of basic instrumentation, such as thermocouples, for a novel application. The system uses the physical properties of the coupling of dissimilar materials, and utilizes two parts, one of the parts being the metering couple. The metering couple is welded on the metallic surface in contact with the hydrogen-generating means which one wants to measure, in such a way as to form a metallurgical continuity with that surface, or bonded to the surface in any other way which allows diffusion of hydrogen through the couple, so as to be subjected to permeation by hydrogen. The other part of the system is the reference couple, attached to the face of the metallic surface in contact with the hydrogen-generating means, so as to form no metallurgical continuity with that surface, so that no hydrogen passes through the surface. The metering couple and the reference couple are both connected to meters of electrical units, such as electrical potential, in that the difference of the electrical units between the couples is a function of the hydrogen mass flow through the surface. In consequence, a process for measuring hydrogen mass flow through a sensor that is easy and cheap to construct and install is obtained. The system can be assembled externally (in such case the metallic surface under permeation by hydrogen being the monitored item's own surface) as well as by insertion (in such case the metallic surface under hydrogen permeation being a thin-wall reaction tube inserted in the process fluid, taking advantage of the lower response time relative to the external assemblage). The system has a very low cost of maintenance, with an unlimited shelf life, and obtains a high response velocity, an accuracy and precision that are equivalent or better than those obtained by the state-of-art methods, and a extremely simple and cheap installation, a low cost of maintenance, with easy integration with process computers, either digital or analog.

DETAILED DESCRIPTION OF THE INVENTION

The principle underlying the present patent is the discovery that the physical properties of a coupling of dissimilar conductors, like those largely used in thermocouples for measuring temperature, on being a function of the different density of electrons in the atomic lattices of each material, are extremely influenced by the flow of atomic hydrogen ($H^0$), which contains one uncoupled electron (represented by the point in the formula H·), through this coupling. To ensure this flow, the measuring couple needs to form a crystalline lattice with metallurgical continuity with the surface to be measured. As the temperature also has an influence over these properties, it is necessary to use a reference couple, made from the same dissimilar materials of the metering couple, in contact with the same surface to be measured, in such a way to remain at the same temperature from the metering couple, eliminating the influence of the temperature over the measured potential. As the potential of the reference couple must only come from temperature, it is necessary that the reference couple not be permeated by hydrogen. So, the reference couple is only attached to the surface to be measured, and, because it does not form a metallurgical continuity with that surface, is not permeated by the hydrogen.

To accomplish the technical concepts that are the basis for the present invention, several experiments were performed using a hydrogen generating cell, volume meter, and proof sensor assembly (see FIG. 2), changing the materials and manufacturing techniques. A hydrogen generation cell (8) in a horizontal cylindrical format was assembled, simulating an item under permeation by hydrogen. This cell contained the surface under permeation (1), in the form of a circular lid, locked by a flange. A current generator (9) was made by connecting a conductor (electrode) (9-A) with a stem in the inner part of the cell, to a potentiostate (9-B), from which another conductor (counterelectrode) (9-C) was connected to the outer face of the surface under permeation (1). The purpose of this potentiostate was to generate electric current to accelerate the formation of hydrogen in the acidic solution contained in the cell. The meter of generated hydrogen volume (10) was assembled by forming a chamber (10-A) in the outer face of the surface under permeation (1), by totally welding a little metallic plate (10-B) spaced from this surface, said plate containing an orifice communicating with an "U" tube (10-C) containing ethylene glycol.

Figure 2:
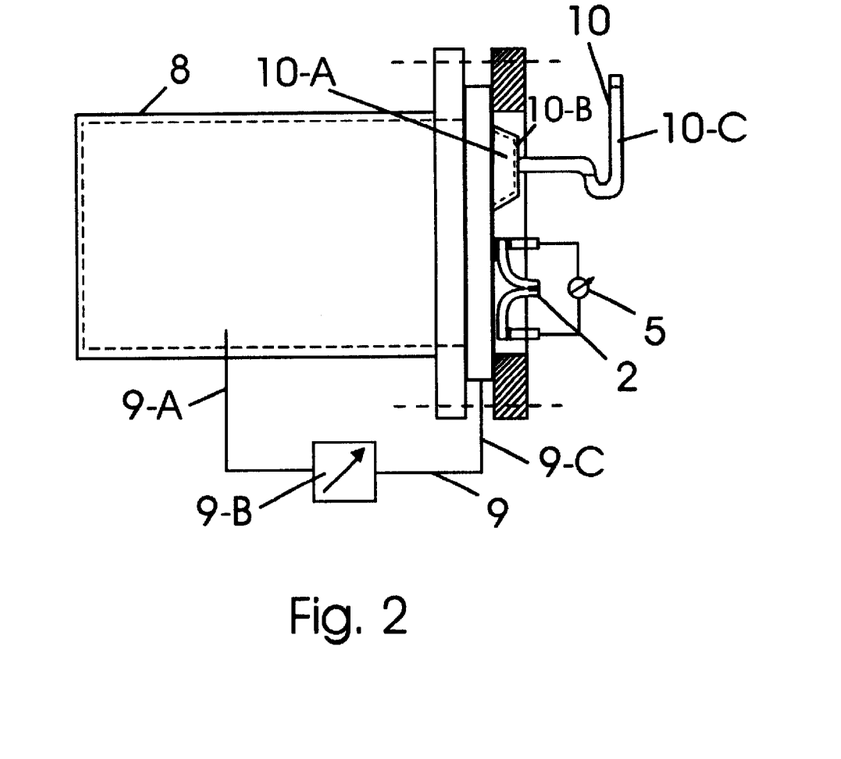
FIG. 2 shows the assembly of the hydrogen generation cell, the volume meter, and proof sensor.

The proof sensor (2) was assembled in two parts in a "U" format (2-A and 2-B), one of the sides (2-A-1 and 2-B-1) and the basis of the "U" (2-A-2 and 2-B-2) being the same material, and the remaining side of the "U" (2-A-3 and 2-B-3) in another material and welded in the basis of the "U", with one of the parts (metering couple) (2-A) welded in the outer face of the lid (1), so as to form a metallurgical continuity with the circular lid (1), and the other part (reference couple) (2-B), only joined by the basis of the "U" (2-B-2) with the outer face of the lid (1), in such way forming no metallurgical continuity between the surfaces. Both sensor parts are connected by metering conductor (3), and reference conductor (4), to a voltmeter that measures electrical difference of potential.

The experiments following described were made, each test repeated thrice, and the results, having a low scattering, were registered on the graph (FIG. 3), relating hydrogen flow by area versus difference of potential between metering couple and reference couple.

Test # 1

Figure 3:
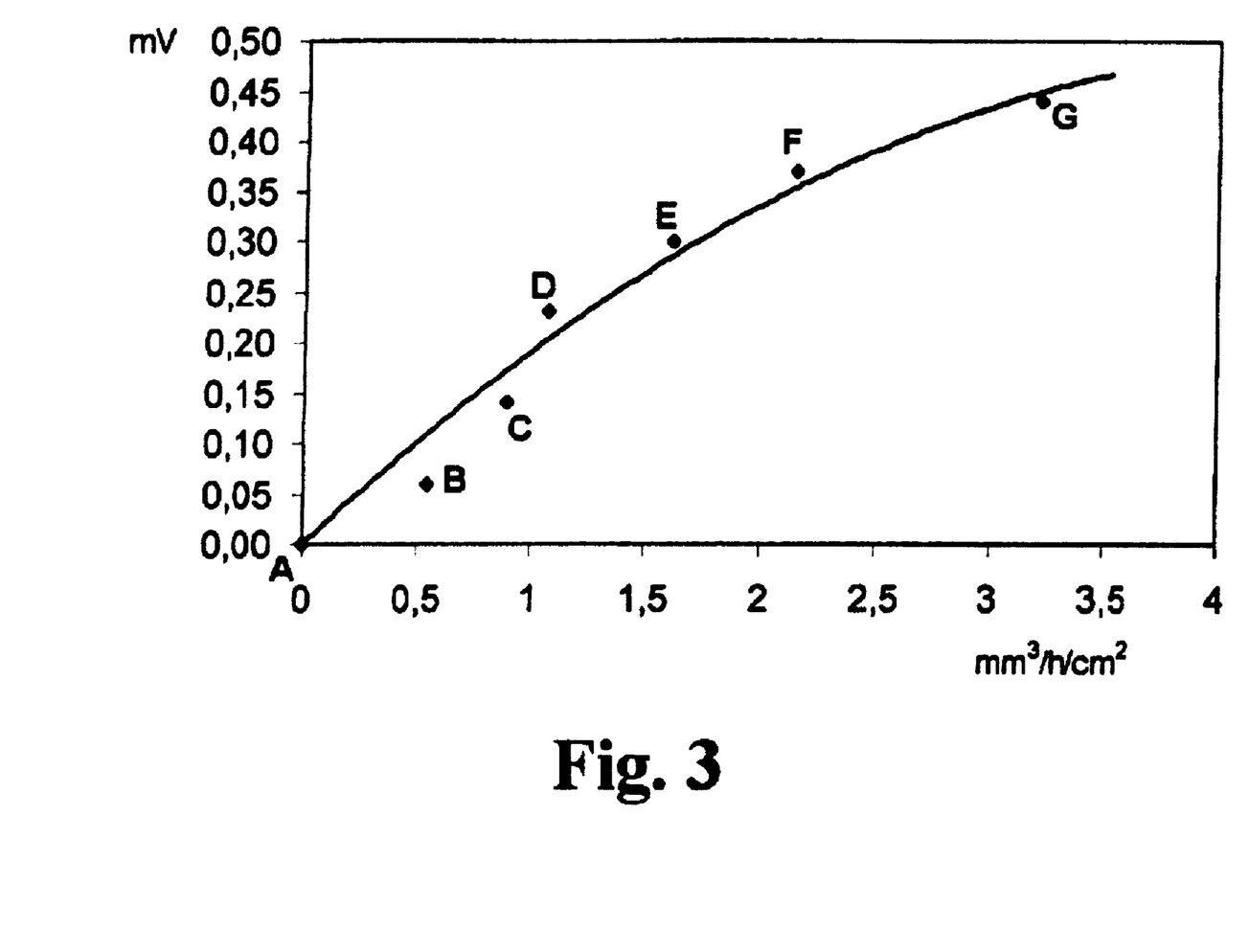
FIG. 3 is a graph correlating hydrogen flow rate by area versus difference-of-potential.

With an empty hydrogen generating cell (8), and with proof sensor (2) made of metering couple (2-A) and reference couple (2-B) with a NiCr—Ni couple, it was measured the voltage at voltmeter (5), for temperatures of 10, 20, 30, 40, 50, 60 and 70 Celsius degrees at the surface under permeation (1), and it was observed that the potential values are practically constant, and equal to zero (see point A, from FIG. 3 graph).

Test # 2

With an empty hydrogen generating cell (8), and with proof sensor (2) made of metering couple (2-A) and reference couple (2-B) with a FE—CuNi couple, it was measured the voltage at voltmeter (5), for temperatures of 10, 20, 30, 40, 50, 60 and 70 Celsius degrees at the surface under permeation (1), and it was observed that the potential values are practically constant, and equal to zero.

Test # 3

With an empty hydrogen generating cell (8), and with proof sensor (2) made of metering couple (2-A) and reference couple (2-B) with a NiCr—NiAl couple, it was measured the voltage at voltmeter (5), for temperatures of 10, 20, 30, 40, 50, 60 and 70 Celsius degrees at the surface under permeation (1), and it was observed that the potential values are practically constant, and equal to zero.

Test # 4

With an empty hydrogen generating cell (8), and with proof sensor (2) made of metering couple (2-A) and reference couple (2-B) with a Pt10-PtRh couple, it was measured the voltage at voltmeter (5), for temperatures of 10, 20, 30, 40, 50, 60 and 70 Celsius degrees at the surface under permeation (1), and it was observed that the potential values are practically constant, and equal to zero.

Test # 5

With an empty hydrogen generating cell (8), and with proof sensor (2) made of metering couple (2-A) and reference couple (2-B) with a Pt30-PtRh couple, it was measured the voltage at voltmeter (5), for temperatures of 10, 20, 30, 40, 50, 60 and 70 Celsius degrees at the surface under permeation (1), and it was observed that the potential values are practically constant, and equal to zero.

Test # 6

With an empty hydrogen generating cell (8), and with proof sensor (2) made of metering couple (2-A) and reference couple (2-B) with a Cu—CuNi couple, it was measured the voltage at voltmeter (5), for temperatures of 10, 20, 30, 40, 50, 60 and 70 Celsius degrees at the surface under permeation (1), and it was observed that the potential values are practically constant, and equal to zero.

Test # 7

With the hydrogen generating cell (8) filled with a 1/3 Molar Acetic Acid aqueous solution, under agitation during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.06 mV, and following the hydrogen generation, it was measured a shift of 1.0 mm/h of ethyleneglycol at column (10-C), which corresponds to a flow of 0.54 $mm^3/h$ of generated hydrogen by $cm^2$ of the surface under hydrogen permeation. (See point B in FIG. 3 graph).

Test # 8

With the hydrogen generating cell (8) filled with a 2/3 Molar Acetic Acid aqueous solution, under agitation during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.14 mV, and following the hydrogen generation, it was measured a shift of 1.6 mm/h of ethyleneglycol at column (10-C), which corresponds to a flow of 0.89 $mm^3/h$ of generated hydrogen by $cm^2$ of the surface under hydrogen permeation. (See point C in FIG. 3 graph).

Test # 9

With the hydrogen generating cell (8) filled with a 1.0 Molar Acetic Acid aqueous solution, under agitation during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.23 mV, and following the hydrogen generation, it was measured a shift of 2.0 mm/h of ethyleneglycol at column (10-C), which corresponds to a flow of 1.07 $mm^3/h$ of generated hydrogen by $cm^2$ of the surface under hydrogen permeation. (See point D in FIG. 3 graph).

Test # 10

With the hydrogen generating cell (8) filled with a 1.0 Molar Acetic Acid aqueous solution, under agitation and under an electrical current of 10 mA, equivalent to 0.2 $mA/cm^2$, supplied by the current generator assembly (9), during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.3 mV, and following the hydrogen generation, it was measured a shift of 3.0 mm/h of ethyleneglycol at column (10-C), which corresponds to a flow of 1.61 $mm^3/h$ of generated hydrogen by $cm^2$ of the surface under hydrogen permeation. (See point E in FIG. 3 graph).

Test # 11

With the hydrogen generating cell (8) filled with a 1.0 Molar Acetic Acid aqueous solution, under agitation and under an electrical current of 20 mA, equivalent to 0.4 mA/cm$^2$, supplied by the current generator assembly (9), during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.37 mV, and following the hydrogen generation, it was measured a shift of 4.0 mm/h of ethyleneglycol at column (10-C), which corresponds to a flow of 2.15 mm$^3$/h of generated hydrogen by cm$^2$ of the surface under hydrogen permeation. (See point F in FIG. 3 graph).

TEST # 12

With the hydrogen generating cell (8) filled with a 1.0 Molar Acetic Acid aqueous solution, under agitation and under an electrical current of 50 mA, equivalent to 1.0 mA/cm$^2$, supplied by the current generator assembly (9), during 48 hours, and with proof sensor (2) made of metering couple (2-A) and reference couple (2-B) with a NiCr—Ni couple, it was measured the voltage at voltmeter (5), at a temperature of 20 Celsius degrees at the surface under permeation (1), and it was observed a potential of 0.44 mV, and following the hydrogen generation, it was measured a shift of 6.0 mm/h of ethyleneglycol at column (10-C), which corresponds to a flow of 3.22 mm$^3$/h of generated hydrogen by cm$^2$ of the surface under hydrogen permeation. (See point G in FIG. 3 graph).

Figure 1:
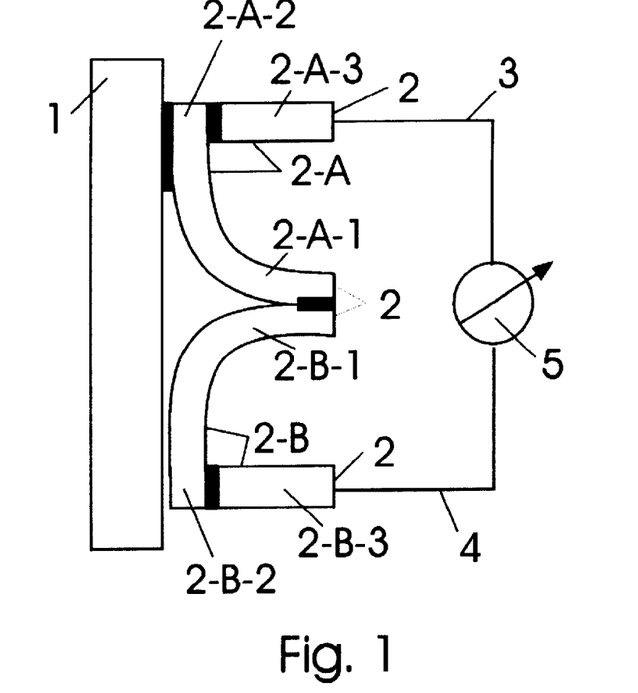
FIG. 1 shows the electrical diagram of the process for metering hydrogen of the present invention.

The process for metering permeated hydrogen flow is realized, in a preferential but not restrictive arrangement, by an apparatus build of a sensor (2), with two parts in an "U" format (2-A and 2-B), being one side (2-A-1 and 2-B-1) and the basis of the "U" (2-A-2 and 2-B-2) made of the same material and the other side of the "U" (2-A-3 and 2-B-3) in another material and welded in the basis of the "U", being one of the parts (metering couple (2-A)) welded by the basis of the "U" (2-A-2) to the outer face of the surface under permeation by hydrogen (1), in a way to form a metallurgical continuity with said surface and the other part (reference couple (2-B)) only attached by the basis of the "U" (2-B-2), in so forming no metallurgical continuity between the surfaces and aiming and allowing the correction of the influence of the temperature over the physical properties of the couple. Both sensor parts are connected by measuring conductor (3) and reference conductor (4) to a voltmeter (5), which measures difference of potential.

The installation of the apparatus for metering hydrogen flow can be made in two ways:

Externally to the Item Under Permeation by Hydrogen a.1.) The basis of the "U" (2-A-2) from the first material is welded on the outer face of the surface under permeation (1), and the side (2-A-3) of the other material is welded in basis (2-A-2), then forming the "U" of the metering couple (2-A) of the sensor (2);

a.2.) The basis of the "U" (2-B-2) of the first material is attached to the outer face of the surface under permeation (1), by ordinary adhesive means that allow an intimate contact with the basis (2-B-2) and the surface under permeation and the obtaining of actual values of temperature at the surface (1), and the side (2-B-3) of the other material is welded on the basis (2-B-2) forming the "U" of the reference couple (2-B) of the sensor (2); and a.3.) The measuring conductor (3) is connected to the side (2-A-3) and the reference conductor (4) is connected to the side (2-B-3), both conductors are connected to the voltmeter (5), and the sides of the "U" (2-A-1 and 2-B-1) are connected each other by welding, or this connection can be made using the same material forming both "U".

Internally to the Item Under Permeation by Hydrogen b.1.) The item is drilled to access its interior. A threaded sleeve is welded, creating a connection. A tubular well from the same material of the item, but with adequate thickness, is screwed in this connection in form of sleeve, in order to maximize the hydrogen permeation.

b.2.) Inside the tubular well the measuring apparatus is implanted, following the same sequence of the items a.1, a.2, and a.3.

It is easily understood by a technically trained person that the present patent is not limited by particular constructive arrangements, such as those presented above, but the employed couples' quantity and materials can be changed, as can the form of these materials and couples, as well as the methods for compensating for the temperature, the measuring instruments, and even the measured electrical variables, without deviating from the scope of this invention, which is the employment of couples of dissimilar materials forming a metering couple and a reference couple, both submitted to the temperature of the item under permeation, said metering couple being under permeation by the hydrogen to be measured, and said reference couple being free from permeation by hydrogen, in a way to utilize the changing in physical properties of the metering couple with the flow of permeated hydrogen to measure this flow, in a way independent from temperature.

What is claimed is:

1. A process for metering hydrogen permeated in a metallurgical structure comprising the steps of:

a) selecting a pair of couples, a metering couple and a reference couple, each said couple being formed from two dissimilar materials, b) setting up a sensor comprising said pair of metering couples, c) positioning said metering couple so that said metering couple has a metallurgical continuity with a metallic surface of said metallurgical structure, thereby ensuring that a flow of hydrogen from a hydrogen-generating means permeates said metering couple, d) positioning said reference couple so that said metering couple has no metallurgical continuity with said metallic surface of said metallurgical structure, thereby ensuring that said flow of hydrogen from said hydrogen-generating means does not permeate said reference couple, e) attaching said metering couple and said reference couple to means of measuring electric characteristics, and f) using a difference in measured electrical characteristics between said metering couple and said reference couple to quantitatively determine a hydrogen mass flow permeating said metallic surface.

2. The method of claim 1 wherein:

said sensor comprises two parts, a first part being formed from a material dissimilar to a material forming said second part, one of said parts comprises a metering couple welded to said metallic surface under permeation by hydrogen such that said one of said parts welded to said metallic surface has metallurgical continuity with said metallic surface, and a second one of said parts has no metallurgical continuity with said metallic surface; and wherein both of said parts are in electrical communication with a measuring device that measures an electrical characteristic of said parts so that a flow rate of hydrogen is quantitatively determined by a difference in said electrical characteristic between said first part and said second part.

3. The method of claim 1 wherein:

said sensor is assembled externally to said metallic surface under permeation by hydrogen, said metering couple being welded to an exterior surface of said metallic surface of said metallurgical structure.

4. The method of claim 1 wherein:

said sensor is assembled internally to said metallic surface under permeation by hydrogen, said sensor being installed in a tube inserted in a hole drilled in said metallic surface of said metallurgical structure.

* * * * *